(12) United States Patent
Philippe et al.

(10) Patent No.: US 6,406,685 B1
(45) Date of Patent: *Jun. 18, 2002

(54) COSMETIC COMPOSITION COMPRISING A COMPOUND SUCH AS INDIGOID

(75) Inventors: Michel Philippe, Wissous; Jean-Christophe Henrion, Pantin; Nathalie Guillier-Berteuil, Brunoy, all of (FR)

(73) Assignee: L'Oreal USA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/554,932

(22) PCT Filed: Nov. 12, 1998

(86) PCT No.: PCT/FR98/02411

§ 371 (c)(1),
(2), (4) Date: Jun. 13, 2000

(87) PCT Pub. No.: WO99/26586

PCT Pub. Date: Jun. 3, 1999

(30) Foreign Application Priority Data

Nov. 21, 1997 (FR) .............................. 97 14656

(51) Int. Cl.[7] ................................. A61K 7/06
(52) U.S. Cl. .................. 424/70.1; 424/401; 424/59; 424/61; 424/64
(58) Field of Search .............. 424/401, 59, 61, 424/64, 70.1, 725

(56) References Cited

U.S. PATENT DOCUMENTS 5,865,853 A * 2/1999 Snhmitt et al. .............. 8/405

FOREIGN PATENT DOCUMENTS

| DE | 44 27 888 | 2/1996 |
|---|---|---|
| DE | 4427888 A1 * | 2/1996 |

OTHER PUBLICATIONS

Kumari, Krishna L., A Simple Synthesis of Diosindigo A, 1982, Indian J. of Chem. Sect. B: Organic and Medicinal Chem., vol. 12B, 755–756.*
Chemical Abstracts, vol. 115, AN–231821.
Chemical Abstracts, vol. 81, AN–91241.
Christine Göltner et al., "2,2'–Binaphthyliden–1,1'–dione—Farbe und Struktur", Liebigs Ann. Chem., vol. 1991, No. 10, Oct. 1991, pp. 1085–1089.
English language Derwent Abstract of DE 44 27 888.

* cited by examiner

*Primary Examiner*—Jose' G. Dees
*Assistant Examiner*—Konata M George
(74) *Attorney, Agent, or Firm*—Finnegan, Henderson, Farabow, Garrett & Dunner LLP

(57) ABSTRACT

A cosmetic composition comprising, in a cosmetically acceptable medium, at least one compound of formula (I)

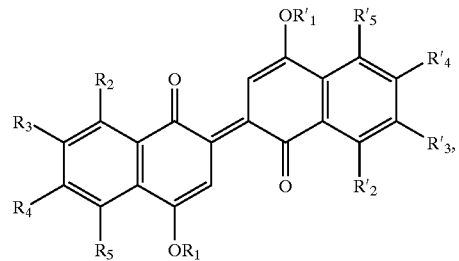

in which $R_1$, and $R'_1$ are chosen from alkyl radicals and $R_2$, $R'_2$, $R_3$, $R'_3$, $R_4$, $R'_4$, $R_5$, and $R'_5$ are chosen from a hydrogen atom, a halogenated radical, a hydroxyl radical, an alkyl, alkyloxy, acyl, or acyloxy radical having 1 to 6 carbon atoms. The use of compounds of formula (I) for coating substrate particles, the resulting powder substance, and its use in a cosmetic composition.

39 Claims, No Drawings

COSMETIC COMPOSITION COMPRISING A COMPOUND SUCH AS INDIGOID

The present invention relates to the use in cosmetics of compounds of indigoid type, in particular for contributing colour to cosmetic compositions.

Cosmetic compositions and in particular make-up compositions, such as loose or compact powders, foundations, face powders, eyeshadows, lipsticks or nail varnishes, are composed of an appropriate vehicle and of various colouring agents intended to confer a certain colour on the said compositions before and/or after their application to the skin, mucous membranes and/or superficial body growths, such as the nails, eyelashes or hair.

A fairly limited range of colouring agents is used today to create colours, among which colouring agents may be mentioned compounds which are generally insoluble in aqueous and organic media, such as organic lakes, inorganic pigments or pearlescent pigments.

The pigments and lakes used in the make-up field are highly varied in origin and in chemical nature. Their physicochemical properties, in particular particle size, specific surface, relative density and the like, are therefore very different. These differences are reflected by variations in behaviour: their ease of use or dispersion in tie medium, their stability with regard to light or to temperature, and their mechanical properties.

Thus, inorganic pigments, in particular inorganic oxides, such as iron oxides, are very stable with regard to light and pH but give rather lifeless, dull and pale colours. It is therefore necessary to introduce a large amount of them into the cosmetic formulations in order to obtain a sufficiently saturated feature. This high percentage of inorganic particles can, nevertheless, affect the gloss of the composition.

Use may also be made, in order to obtain coloured effects, of pearlescent pigments of varied but never very intense colours, which make it possible to obtain iridescent but mostly fairly weak effects.

In the field of temporary or transient hair colouring, which gives rise to a slight modification of the natural colour of the hair which lasts from one shampooing to another and which serves to beautify or correct a shade which has already been obtained, provision has already been made for colouring with conventional inorganic pigments, in order to introduce a temporary highlight to the hair, but the shades obtained by this colouring remain fairly lifeless, too uniform and not very playful.

In the field of make-up, only organic lakes have until now made it possible to obtain vivid and intense colours. However, most organic lakes exhibit very poor hold with regard to light, which results in a very marked attenuation in their colour over time. They can also be unstable with regard to temperature and/or pH. Furthermore, some lakes result in an excessive degree of bleeding, that is to say that they exhibit the disadvantage of staining the support to which they are applied. Thus, this can have the consequence of staining ocular lenses, in the case of eyeliners or mascaras, or of leaving a colouring on the skin or nails after the removal of make-up, in the case of lipsticks or nail varnishes. Finally, the instability of lakes is further exacerbated when they are used in combination with photoreactive pigments, such as titanium dioxide. In point of fact, these pigments are very widely used in make-up, in particular for protection against UV radiation. Consequently, the use of organic lakes in cosmetics is fairly limited, the consequence of which is a limitation in the tints achievable.

Thus, the need remains to have available colouring agents which can be used in cosmetics and which make it possible to obtain an appropriate colouring of the compositions and of the make-up film obtained, it being necessary for the said colouring agents not to bleed onto the support on which the said compositions are deposited.

After much research, the Applicant Company has demonstrated that the use of a very specific family of organic compounds makes it possible to obtain such a result.

Thus, a subject-matter of the invention is a cosmetic composition comprising, in a cosmetically acceptable medium, at least one compound of formula (I):

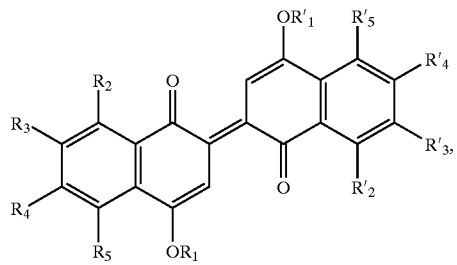

in which
  $R_1$ and $R'_1$ are, independently of one another, saturated or unsaturated, linear, branched or cyclic alkyl radicals having 1 to 18 carbon atoms which are optionally substituted by one or more halogens and/or by one or more hydroxyl radicals and/or interrupted by one or more heteroatoms;
  $R_2$, $R'_2$, $R_3$, $R'_3$, $R_4$, $R'_4$, $R_5$ and $R'_5$ are, independently of one another, chosen from a hydrogen atom, a halogenated radical, a hydroxyl radical or a saturated or unsaturated, linear or branched, alkyl, alkyloxy, acyl or acyloxy radical having 1 to 6 carbon atoms.

Another subject-matter of the invention is the use of at least one compound of formula (I) for at least partially coating substrate particles.

Another subject-matter of the invention is a pulverulent material composed of substrate particles which are at least partially coated with at least one compound (I).

Yet another subject-matter of the invention is the use of at least one compound of formula (I) and/or of at least one pulverulent material as defined above as colouring agent, in particular in a cosmetic composition.

Another subject-matter of the invention is a cosmetic composition comprising, in a cosmetically acceptable medium, at least one pulverulent material as defined above.

The compounds used in the context of the invention are, in some cases, compounds known in the literature. Some have been disclosed in particular in the publication "2,2'-Binaphthyliden-1,1'-dione, Farbe und Struktur" [2,2'-Binaphthylidene-1,1'-dione, Colour and Structure] by G öltner et al., Liebigs Ann. Chem., 1991, pages 1085–1089. This publication discloses in particular a preparation process which makes it possible to obtain some of these compounds in the form of crystals with a mauve colour or blue colour ranging from pale blue to dark blue.

However, there is nothing in this publication which allows it to be envisaged that these compounds can be employed with success in cosmetic compositions, that is to say that they make possible the preparation of a cosmetically acceptable composition capable of being applied to the skin, the said composition not bleeding.

It is to the credit of the Applicant Company to have found that such a use is possible.

It has also been found that, in addition, it is possible to adjust the colour of the compounds of formula (I) by varying the nature and/or the position of the various R substituents present on the molecule.

It is thus possible to obtain compounds with a colour which can vary from mauve to red, passing through blue and green.

Furthermore, the compounds used in the context of the invention exhibit good stability with regard to temperature, pH and light.

They are also readily accessible by chemical synthesis, even on an industrial scale.

The compounds used according to the invention therefore have the following formula (I):

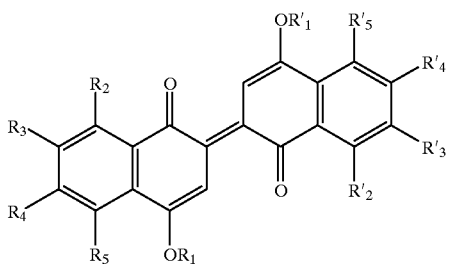

in which

R$_1$ and R'$_1$ are, independently of one another, saturated or unsaturated, linear, branched or cyclic alkyl radicals having 1 to 18 carbon atoms which are optionally substituted by one or more halogens and/or by one or more hydroxyl radicals and/or interrupted by one or more heteroatoms;

R$_2$, R'$_2$, R$_3$, R'$_3$, R$_4$, R'$_4$, R$_5$ and R'$_5$ are, independently of one another, chosen from a hydrogen atom, a halogenated radical, a hydroxyl radical or a saturated or unsaturated, linear or branched, alkyl, alkyloxy, acyl or acyloxy radical having 1 to 6 carbon atoms.

Mention may be made, among the heteroatoms, of the oxygen, silicon, nitrogen or sulphur atoms (O, Si, N or S).

R$_1$ and/or R'$_1$ are preferably alkyl radicals having 1 to 8 carbon atoms and in particular methyl, CA ethyl, propyl, isopropyl, butyl, pentyl or hexyl radicals. R$_1$ and R'$_1$ preferably represent the same radical.

R$_2$ to R$_5$ and R'$_2$ to R'$_5$ preferably represent a hydrogen atom.

In particular, mention may be made, as compounds capable of being used according to the invention, of the following compounds:

4,4'-dimethyloxy-[2,2'-binaphthylidene]-1,1'-dione,
4,4'-diethyloxy-[2,2'-binaphthylidene]-1,1'-dione,
4,4'-diisopropyloxy-[2,2'-binaphthylidene]-1,1'-dione, and
4,4'-di(n-hexyloxy)-[2,2'-binaphthylidene]-1,1'-dione.

The compounds of formula (I) are provided in solid form. They produce vivid and varied colours, according to the nature of the substituents.

They are generally insoluble in water and have very little solubility in oils of varied nature and/or polarity. These compounds consequently exhibit the advantage of showing very little bleeding when they are used in compositions comprising fatty substances.

The compounds according to the invention can be easily prepared by a person skilled in the art on the basis of the prior art and of his general technical knowledge.

The compounds of formula (I) can be incorporated in a composition, in particular a cosmetic composition, in an amount which can be easily determined by a person skilled in the art on the basis of his general knowledge and which can in particular be between 0.1 and 80% by weight with respect to the total weight of the composition, preferably in an amount of 0.5 to 70% by weight, more preferably in an amount of 1 to 50% by weight, for example in an amount of 2 to 20% by weight.

The said compounds can be present in the composition in the free form or in the form of a combination with substrate particles, which they coat.

This is because it has been found that the compounds of formula (I) exhibit the distinguishing feature of being able to coat, at least partially, indeed even completely, substrate particles such as conventional pigments or fillers.

Mention may in particular be made, among particles capable of being coated by the compounds of formula (I), of metal oxide pigments or nanopigments, such as titanium, zinc, iron, manganese, cerium and/or zirconium oxides; white fillers, such as talc, mica, silica, kaolin, or nylon and polyethylene powders; or microspheres, such as hollow microspheres formed of vinylidene chloride/acrylonitrile copolymers.

Talc is preferably chosen as substrate particle to be coated.

The pulverulent materials thus obtained, composed of the coated substrate particles, can then themselves be used as colouring agent in compositions, in particular cosmetic compositions.

It has been found that the said pulverulent materials exhibit, under electron microscopy, a very homogeneous structure.

It has also been found that the said pulverulent materials can exhibit the properties and advantages of each of the starting materials; in particular, when talc, known to contribute softness, is coated, a coated talc is obtained which retains its softness.

Furthermore, the use of a very small amount of compound of formula (I) coating a conventional filler makes it possible to obtain a colouring agent which has a high colouring strength, even used in a small amount, and which contributes appropriate coverage, as well as a colour having good hold with regard to light.

Use will preferably be made of the compounds of formula (I) in an amount of 0.1 to 100 parts by weight per 100 parts by weight of substrate particles to be coated.

The coated pulverulent material is preferably composed of 1 to 20% by weight of compounds of formula (I) and of 80 to 99% by weight of substrate particles. However, it is possible to envisage a coated pulverulent material composed of 50% by weight of compounds of formula (I) and of 50% by weight of substrate particles.

The pulverulent material, composed of substrate particles which are at least partially coated with the compound of formula (I), will generally be prepared in the following way:

in a first step, the compound of formula (I) is dissolved in an appropriate solvent, for example DMF, then the said compound is precipitated on the substrate particle to be coated, for example by adding the solution of the said compound to an aqueous dispersion or suspension of the said particle.

The pulverulent material can subsequently be filtered off, washed and dried according to conventional techniques.

The said compounds of formula (I) and/or the said pulverulent materials can be used in particular as colouring agent in a cosmetic composition which can be provided in the form of a product to be applied to the mucous membranes, semi-mucous membranes and/or keratinous materials, such as the skin and superficial body growths (nails, eyelashes, eyebrows and hair, including body hair). The said composition therefore comprises a cosmetically acceptable medium, that is to say a medium compatible with all keratinous substances, such as the skin, nails, hair, eyelashes and eyebrows, mucous membranes and semi-mucous membranes, and any other cutaneous region of the body and face. The said medium can comprise or be provided in the form of, in particular, a suspension, a dispersion or a solution in solvent or aqueous/alcoholic medium which is optionally thickened, indeed even gelled; an oil-in-water, water-in-oil or multiple emulsion; a gel or a foam; an emulsified gel; a dispersion of vesicles, in particular lipid vesicles; a two-phase or multiphase lotion; a spray; a loose, compact or cast powder; or an anhydrous paste. A person skilled in the art can choose the appropriate pharmaceutical dosage form, as well as its method of preparation, on the basis of his general knowledge, taking into account, on the one hand, the nature of the constituents used, in particular their solubility in the vehicle, and, on the other hand, the application envisaged for the composition.

When the composition is provided in the aqueous form, in particular in the form of an aqueous dispersion, emulsion or solution, it can comprise an aqueous phase, which can comprise water, a floral water and/or a mineral water.

The said aqueous phase can comprise from 0% to 14% by weight, with respect to the total weight of the aqueous phase, of a lower $C_2$–$C_6$ monoalcohol and/or of a polyol, such as glycerol, butylene glycol, isoprene glycol, propylene glycol or polyethylene glycol.

When the composition according to the invention is provided in the form of an emulsion, it can, in addition, optionally comprise a surfactant, preferably in an amount of 0.01 to 30% by weight with respect to the total weight of the composition. The composition according to the invention can also comprise 0 to 5% by weight, with respect to the total weight of emulsion, of at least one coemulsifier, which can be chosen from oxyethylenated sorbitan monostearate, fatty alcohols, such as stearyl alcohol or cetyl alcohol, or esters of fatty acids and of polyols, such as glyceryl stearate.

The composition according to the invention can also comprise one or more thickening agents in concentrations preferably ranging from 0 to 6% by weight, with respect to the total weight of the composition, chosen from:

polysaccharide biopolymers, such as xanthan gum, locust bean gum, guar gum, alginates, modified celluloses, starch derivatives, cellulose ether derivatives possessing quaternary ammonium groups, or cationic polysaccharides;

synthetic polymers, such as poly(acrylic acid)s, polyvinylpyrrolidone, poly(vinyl alcohol) or polymers based on polyacrylamide;

aluminium magnesium silicate.

Depending on the application envisaged, the composition can additionally comprise a film-forming polymer. This is in particular the case when it is desired to prepare a composition of nail varnish, mascara or eyeliner type or a hair composition of lacquer type. The polymers can be dissolved or dispersed in the cosmetically acceptable medium. In particular, the polymer can be present in the form of a solution in an organic solvent or in the form of an aqueous dispersion of particles of film-forming polymer. The said polymer can be chosen from nitrocellulose, cellulose acetobutyrate, poly(vinyl butyral)s, alkyd resins, polyesters, acrylics, vinyls and/or polyurethanes.

The composition can also comprise at least one plasticizer, which can be present at a content ranging from 1% to 40% by weight with respect to the total weight of the composition.

The composition according to the invention can also comprise a fatty phase composed in particular of fatty substances which are liquid at 25° C., such as oils of animal, vegetable, mineral or synthetic origin; of fatty substances which are solid at 25° C, such as waxes of animal, vegetable, mineral or synthetic origin; of pasty fatty substances; of gums; or of their mixtures.

The compositions according to the invention can thus comprise volatile oils which will evaporate on contact with the skin but the presence of which in the cosmetic composition is of use as they facilitate the spreading of the composition during application to the skin. Such spreading agents, here known as "volatile oils", are generally oils having a saturated vapour pressure at 25° C. at least equal to 0.5 millibar (i.e. 50 Pa)

Mention may thus be made of volatile silicone oils, such as:

cyclic volatile silicones having from 3 to 8 silicon atoms and preferably from 4 to 6, cyclocopolymers of the dimethylsiloxane/methylalkylsiloxane type, linear volatile silicones having from 2 to 9 silicon atoms.

Mention may also be made of volatile hydrocarbonaceous oils, such as isoparaffins, in particular isododecane, and fluorinated oils.

Use may also be made of nonvolatile oils, among which may be mentioned:

poly($C_1$–$C_{20}$)alkylsiloxanes and in particular those with end trimethylsilyl groups, preferably those with a viscosity of less than 0.06 m²/s, among which may be mentioned linear polydimethylsiloxanes and also alkylmethylpolysiloxanes, such as cetyl dimethicone (CTFA name), silicones modified by optionally fluorinated aliphatic and/or aromatic groups or by functional groups, such as hydroxyl, thiol and/or amine groups, phenylated silicone oils, in particular those of formula:

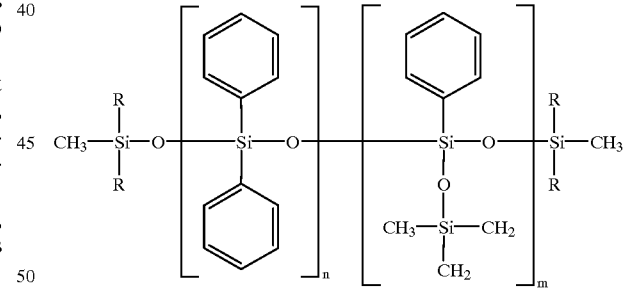

in which R is a $C_1$–$C_{30}$ alkyl radical, an aryl radical or an aralkyl radical, n is an integer of between 0 and 100 and m is an integer of between 0 and 100, with the proviso that the sum is between 1 and 100, oils of animal, vegetable or mineral origin and in particular animal or vegetable oils formed by fatty acid esters of polyols, in particular liquid triglycerides, for example sunflower, maize, soybean, cucumber, grape seed, sesame, hazelnut, apricot, almond or avocado oils; fish oils, capric/caprylic triglyceride, or vegetable or animal oils of formula $R_1COOR_2$ in which $R_1$ represents the residue of a higher fatty acid comprising from 7 to 19 carbon atoms and $R_2$ represents a branched hydrocarbonaceous chain comprising from 3 to 20 carbon atoms, for example Purcellin oil; liquid paraffin, liquid petrolatum, perhydrosqualene, or wheat germ, calophyllum, sesame, macadamia, grape seed, rapeseed, coconut, groundnut, palm, castor, jojoba, olive or cereal germ oils; fatty acid esters; alcohols; acetylglycerides; octanoates, decanoates or ricinoleates of alcohols or polyalcohols; fatty acid triglycerides; or glycerides;

fluorinated and perfluorinated oils.

The composition according to the invention can additionally comprise other fatty substances, which can be chosen by a person skilled in the art on the basis of his general knowledge, so as to confer the desired properties, for example of consistency and/or of texture, on the final composition. These additional fatty substances can be waxes, gums and/or pasty fatty substances of animal, vegetable, mineral or synthetic origin, and their mixtures.

Mention may in particular be made of:

silicone gums, waxes of animal, vegetable, mineral or synthetic origin, such as microcrystalline waxes, paraffin wax, petrolatum wax, ozokerite or montan wax; beeswax or lanolin and its derivatives; candelilla, ouricury, carnauba or japan waxes, cocoa butter or cork fibre or sugar cane waxes; hydrogenated oils which are solid at 25° C., ozokerites or fatty esters and glycerides which are solid at 25° C.; polyethylene waxes and waxes obtained by the Fischer-Tropsch synthesis; hydrogenated oils which are solid at 25° C.; lanolins; fatty esters which are solid at 25° C.; silicone waxes; or fluorinated waxes.

The composition according to the invention can also comprise one or more cosmetically acceptable organic solvents (acceptable tolerance, toxicology and feel). These organic solvents can represent from 0% to 98% of the total weight of the composition and can be chosen from the group consisting of hydrophilic organic solvents, lipophilic organic solvents, amphiphilic solvents or their mixtures.

In addition, the composition can comprise a particulate phase, which can comprise pigments and/or pearlescent agents and/or fillers commonly used in cosmetic compositions. The term "pigments" should be understood as meaning white or coloured, inorganic or organic particles intended to colour and/or opacify the composition. The term "fillers" should be understood as meaning colourless or white, inorganic or synthetic, lamellar or non-lamellar particles intended to give body or stiffness to the composition and/or softness, mattness and uniformity to the make-up. The term "pearlescent agents" should be understood as meaning iridescent particles which reflect light.

The pigments can be present in the composition in a proportion of 0 to 15% by weight of the final composition and preferably in a proportion of 8 to 10% by weight. They can be white or coloured, inorganic and/or organic, and of conventional or nanometric size. Mention may be made of titanium, zirconium or cerium dioxides, as well as zinc, iron or chromium oxides, ferric blue, chromium hydrate, carbon black, ultramarines (aluminosilicate polysulphides), manganese pyrophosphate and some metal powders, such as silver or aluminium powders. Mention may also be made of lakes commonly employed to confer a make-up effect on the lips and skin, which lakes are calcium, barium, aluminium or zirconium salts, or acid dyes.

The pearlescent agents can be present in the composition in a proportion of 0 to 20% by weight, preferably at a level of the order of 8 to 15% by weight. Mention may be made, among pearlescent agents which can be envisaged, of natural mother-of-pearl, mica covered with titanium oxide, with iron oxide, with natural pigment or with bismuth oxychloride, and coloured titanium oxide-coated mica.

The fillers, which can be present in a proportion of 0 to 30% by weight, preferably 5 to 15%, in the composition, can be inorganic or synthetic, lamellar or non-lamellar. Mention may be made of talc, mica, silica, kaolin, nylon and polyethylene powders, Teflon, starch, boron nitride, polymer microspheres, such as Expancel (Nobel Industrie), polytrap (Dow Corning) and silicone resin microbeads (Tospearls from Toshiba, for example), precipitated calcium carbonate, magnesium carbonate or hydrated magnesium carbonate, or metal soaps derived from organic carboxylic acids having from 8 to 22 carbon atoms.

Depending on the type of formulation, the pulverulent phase can represent from 0.01 to 99% by weight of the composition.

In addition, the composition can comprise a dye, in particular a natural organic dye, such as cochineal carmine, and/or a synthetic dye, such as haloacid, azo or anthraquinone dyes. Mention may also be made of inorganic dyes, such as copper sulphate.

In addition, the composition can comprise any additive normally used in the cosmetics field, such as antioxidants, fragrances, essential oils, preservatives, lipophilic or hydrophilic cosmetic active principles, moisturizers, vitamins, essential fatty acids, sphingolipids, self-tanning agents, such as DHA, sunscreen agents, antifoaming agents or sequestering agents.

Of course, a person skilled in the art will take care to choose the optional additional compounds and/or their amount so that the advantageous properties of the composition according to the invention are not, or not substantially, detrimentally affected by the envisaged addition.

The cosmetic compositions according to the invention can be provided in the form of a care and/or make-up product for the skin, an antisun or self-tanning product, or a hair product.

In particular, they find a particular application in the make-up field, in particular as lipsticks, foundations, face powders, eyeshadows, loose or compact powders, eyeliners, mascaras or nail varnishes.

The invention is illustrated in more detail in the following examples.

EXAMPLE 1

Preparation of 4,4'-dimethyloxy-[2,2'-binaphthylidene]-1,1'-dione 10 g of 4-methoxy-1-naphthol are dissolved, at room temperature, in a mixture of 1 litre of dimethylacetamide, 250 ml of methanol and 150 ml of water.

31 g (2 equivalents) of ferric chloride hexahydrate are added, with stirring.

The mixture is left stirring for 5 minutes and then the blue precipitate is filtered off on sintered glass.

The compound is washed and dried in the usual way.

5.2 g (yield: 52%) of the desired pigment are obtained in the form of a blue/purple amorphous powder.

Melting point: 274° C.

HPTLC ($CH_2Cl_2$) : single-spot profile, $R_f$=0.7

HPLC: single-peak profile

Mass, NMR and UV spectra: in accordance with the expected structure.

| Elemental analysis: | | | |
|---|---|---|---|
| | C % | H % | O % |
| Theoretical | 76.73 | 4.68 | 18.20 |
| Experimental | 76.94 | 4.64 | 18.53 |

The stability of this compound is tested and the following results are obtained:

stability at 90° C.: at least 16 hours stability at 45° C.: at least 1 month stability at pH 4: at least 1 month stability at pH 10: at least 1 month stability with regard to light (Suntest): at least 36 hours.

EXAMPLE 2

Preparation of 4,4'-diethyloxy-[2,2'-binaphthylidene]-1,1'-dione 20 g of 4-ethoxy-1-naphthol are dissolved, at room temperature, in 500 ml of chloroform.

19 g of silver oxide are added, with stirring, and the reaction mixture is left stirring for 1 hour. The precipitate is filtered off on sintered glass and washed with refluxing dichloromethane until the solvent is no longer coloured, the organic phase is concentrated and crystals with a dark purple colour are obtained, which crystals are dried.

10 g (yield: 50%) of the desired pigment are obtained in the form of crystals.

Melting point: 244° C.

HPTLC (CH$_2$Cl$_2$): single-spot profile, R$_f$=0.8

NMR spectrum: in accordance with the expected structure.

| Elemental analysis: | | | |
|---|---|---|---|
| | C % | H % | O % |
| Theoretical | 77.40 | 5.41 | 17.18 |
| Experimental | 77.46 | 5.30 | 17.03 |

EXAMPLE 3

Preparation of 4,4'-diisopropyloxy-[2,2'-binaphthylidene]-1,1'-dione

The preparation is carried out in a similar way to Example 2, from 20 g of 4-isopropyl-1-naphthol and 20 g of silver oxide.

16.4 g of purple crystals are obtained (yield: 83%).

Melting point: 230° C.

HPTLC (dichloromethane 8/heptane 2): single-spot profile, R$_f$=0.5

NMR spectrum: in accordance with the expected structure.

| Elemental analysis: | | | |
|---|---|---|---|
| | C % | H % | O % |
| Theoretical | 77.98 | 6.04 | 15.98 |
| Experimental | 78.41 | 6.10 | 15.58 |

EXAMPLE 4

Preparation of 4,4'-di(n-hexyloxy)-[2,2'-binaphthylidene]-1,1'-dione

The preparation is carried out in a similar way to Example 2, from 7 g of 4-(n-hexyl)-1-naphthol and 14 g of silver oxide.

6.0 g of purple crystals are obtained (yield: 86%).

Melting point: 146° C.

HPTLC (dichloromethane 4/heptane 6): single-spot profile, R$_f$=0.2

NMR spectrum: in accordance with the expected structure.

EXAMPLE 5

Coating with Talc 0.6 g of 4,4'-dimethyloxy-[2,2'-binaphthylidene]-1,1'-dione is dissolved under warm conditions in 100 ml of dimethylformamide. This mixture is run slowly onto a vigorously stirred suspension of 20 g of talc in 200 ml of water. The suspension is allowed to cool to room temperature, filtered on sintered glass, washed with water and dried.

A pigment with a light blue homogeneous colour is obtained, which pigment is supported at 3% by weight on the talc.

EXAMPLE 6

2.05 g of 4,4'-dimethyloxy-[2,2'-binaphthylidene]-1,1'-dione are dissolved under warm conditions in 410 ml of dimethylformamide. This mixture is run slowly onto a vigorously stirred suspension of 20.5 g of talc in 820 ml of water. The suspension is allowed to cool to room temperature, filtered on sintered glass, washed with water and dried.

A pigment with a blue homogeneous colour is obtained, which pigment is supported at 10% by weight on the talc.

EXAMPLE 7

4.1 g of 4,4'-dimethyloxy-[2,2'-binaphthylidene]-1,1'-dione are dissolved under warm conditions in 820 ml of dimethylformamide. This mixture is run slowly onto a vigorously stirred suspension of 20.5 g of talc in 1640 ml of water. The suspension is allowed to cool to room temperature, filtered on sintered glass, washed with water and dried.

A pigment with a dark blue homogeneous colour is obtained, which pigment is supported at 20% by weight on the talc.

EXAMPLE 8

An eyeshadow is prepared comprising the following ingredients:

| | |
|---|---|
| talc | 38 g |
| mica | 20 g |
| bismuth oxychloride | 8 g |
| zinc stearate | 3 g |
| nylon powder | 20 g |
| compound of Example 1 | 5 g |
| fatty binder | q.s. for 100 g |

A blue eyeshadow is obtained.

EXAMPLE 9

A mascara is prepared comprising the following ingredients:

| | |
|---|---|
| stearic acid | 6 g |
| glyceryl stearate | 3.5 g |
| beeswax | 5.5 g |
| carnauba wax | 2 g |
| paraffin wax | 7.5 g |
| preservatives | q.s. |
| triethanolamine | 3 g |
| acacia gum | 6 g |
| compound of Example 1 | 5 g |
| water | q.s. for 100 g |

A blue-coloured mascara is obtained.

What is claimed is:

1. A cosmetic composition comprising, in a cosmetically acceptable medium, at least one compound of formula(I):

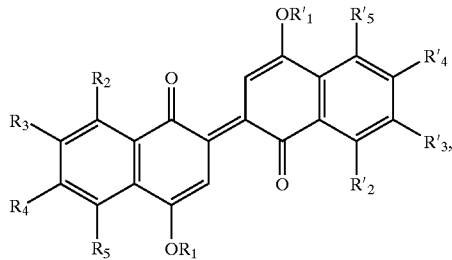

in which
- $R_1$ and $R'_1$ are, independently of one another, saturated or unsaturated, linear, branched or cyclic alkyl radicals having 1 to 18 carbon atoms optionally substituted by at least one substituent chosen from halogens and hydroxyl radicals and optionally interrupted by one or more heteroatoms;
- $R_2$, $R'_2$, $R_3$, $R'_3$, $R_4$, $R'_4$, $R_5$ and $R'_5$ are, independently of one another, chosen hydrogen atom, a halogenated radical, a hydroxyl radical and a saturated or unsaturated, linear or branched, alkyl, alkyloxy, acyl or acyloxy radical having 1 to 6 carbon atoms;
    wherein said at least one compound of formula (I) is present in said composition in an amount effective to be applied to a hair or skin surface with little or no bleeding onto the surface.

2. A composition according to claim 1, in which said at least one of $R_1$ and $R'_1$ radicals are alkyl radicals having 1 to 8 carbon atoms.

3. A composition according to claim 2, in which said $R_2$, $R'_2$, $R_3$, $R'_3$, $R_4$, $R'_4$, $R_5$ and $R'_5$ are hydrogen atoms.

4. A composition according to claim 1, in which said $R_2$, $R'_2$, $R_3$, $R'_3$, $R_4$, $R'_4$, $R_5$ and $R'_5$ are hydrogen atoms.

5. A composition according to claim 1, in which said at least one compound of formula (I) is chosen from:

4,4'-dimethyloxy-[2,2'-binaphthylidene]-1,1'-dione, 4,4'-diethyloxy-[2,2'-binaphthylidene]-1,1'-dione, 4,4'-diisopropyloxy-[2,2'-binaphthylidene]-1,1'-dione, and 4,4'-di(n-hexyloxy)-[2,2'-binaphthylidene]-1,1'-dione.

6. A composition according to claim 1, in which said at least one compound of formula (I) is present in an amount ranging from 0.1 to 80% by weight with respect to the total weight of the composition.

7. A composition according to claim 6 in which said at least one compound of formula (I) is present in an amount ranging from 0.5 to 70% by weight with respect to the total weight of the composition.

8. A composition according to claim 1, in which said at least one compound of formula (I) is present in the free form or in the form of a combination with substrate particles, which it coats.

9. A composition according to claim 8, in which the substrate particles are chosen from metal oxide pigments or nanopigments, fillers and microspheres.

10. A composition according to claim 9, in which said fillers are chosen from talc, mica, silica, kaolin, and nylon and polyethylene powders.

11. A composition according to claim 9, in which said microspheres are chosen from hollow microspheres formed of vinylidene chloride/acrylonitrile copolymers.

12. A composition according to claim 1, in which the cosmetically acceptable medium is in the form of a suspension, a dispersion or a solution in solvent or aqueous/alcoholic medium optionally thickened; an oil-in-water, water-in-oil or multiple emulsion; a gel or a foam; an emulsified gel; a dispersion of vesicles; a two-phase or multiphase lotion; a spray; a loose, compact or cast powder; or an anhydrous paste.

13. A composition according to claim 12, in which said optionally thickened medium is a gelled medium.

14. A composition according to claim 12, in which said vesicles are lipid vesicles.

15. A composition according to claim 1, wherein said composition is in the form of a care and/or make-up product for the skin, an antisun or self-tanning product, or a hair product.

16. A composition according to claim 1, wherein said composition is in the form of a lipstick, a foundation, a face powder, an eyeshadow, a loose or compact powder, an eyeliner, a mascara or a nail varnish.

17. A composition according to claim 16, wherein said composition is in the form of a face powder or an eyeshadow.

18. A method of at least partially coating substrate particles comprising adding to said substrate particles at least one compound of formula (I)

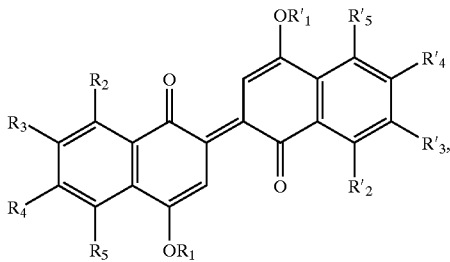

in which

R$_1$ and R'$_1$ are, independently of one another, saturated or unsaturated, linear, branched or cyclic alkyl radicals having 1 to 18 carbon atoms optionally substituted by at least one substituent chosen from halogens and hydroxyl radicals and optionally interrupted by one or more heteroatoms;

R$_2$, R'$_2$, R$_3$, R'$_3$, R$_4$, R'$_4$, R$_5$ and R'$_5$ are, independently of one another, chosen from a hydrogen atom, a halogenated radical, a hydroxyl radical and a saturated or unsaturated, linear or branched, alkyl, alkyloxy, acyl or acyloxy radical having 1 to 6 carbon atoms.

19. A method according to claim 18, in which said substrate particles are chosen from pigments, fillers and microspheres.

20. A method according to claim 19, in which said pigments are chosen from metal oxide pigments and nanopigments.

21. A method according to claim 20, in which said metal oxide pigments or nanopigments are chosen from titanium, zinc, iron, manganese, cerium and zirconium oxides.

22. A method according to claim 19, in which said fillers are chosen from talc, mica, silica, kaolin, and nylon and polyethylene powders.

23. A method according to claim 19, in which said microspheres are chosen from hollow microspheres formed of vinylidene chloride/acrylonitrile copolymers.

24. A pulverulent material composed of substrate particles, in which said substrate particles are at least partially coated with at least one compound of formula (I)

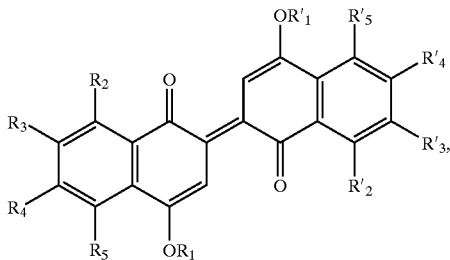

in which

R$_1$ and R'$_1$ are, independently of one another, saturated or unsaturated, linear, branched or cyclic alkyl radicals having 1 to 18 carbon atoms optionally substituted by at least one substituent chosen from halogens and hydroxyl radicals and optionally interrupted by one or more heteroatoms;

R$_2$, R'$_2$, R$_3$, R'$_3$, R$_4$, R'$_4$, R$_5$ and R'$_5$ are, independently of one another, chosen from a hydrogen atom, a halogenated radical, a hydroxyl radical and a saturated or unsaturated, linear or branched, alkyl, alkyloxy, acyl or acyloxy radical having 1 to 6 carbon atoms.

25. A pulverulent material according to claim 24, which said substrate particles are chosen from pigments, fillers and microspheres.

26. A pulverulent material according to claim 25, in which said pigments are chosen from metal oxide pigments and nanopigments.

27. A pulverulent material according to claim 26, in which said metal oxide pigments and nanopigments are chosen from titanium, zinc, iron, manganese, cerium and zirconium oxides.

28. A pulverulent material according to claim 25, in which said fillers are chosen from talc, mica, silica, kaolin, and nylon and polyethylene powders.

29. A pulverulent material according to claim 25, in which said microspheres are chosen from hollow microspheres formed of vinylidene chloride/acrylonitrile copolymers.

30. A pulverulent material according to claim 24, in which said compounds of formula (I) are present in an amount of 0.1 to 100 parts by weight per 100 parts by weight of substrate particles to be coated.

31. A pulverulent material according to claim 24, in which said at least one compound of formula (I) is present in an amount ranging from 1 to 50% by weight of the pulverulent material, and said substrate particles are present in an amount ranging from 50 to 99% by weight of the pulverulent material.

32. A pulverulent material according to claim 31, in which said at least one compound of formula (I) is present in an amount ranging from 1 to 20% by weight of the pulverulent material, and said substrate particles are present in an amount ranging from 80 to 99% by weight of the pulverulent material.

33. A cosmetic composition comprising, in a cosmetically acceptable medium, at least one pulverulent material according to claim 24.

34. A composition according to claim 33, wherein said composition is in the form of a care and/or make-up product for the skin, an antisun or self-tanning product, or a hair product.

35. A composition according to claim 33, wherein said composition is in the form of a lipstick, a foundation, a face powder, an eyeshadow, a loose or compact powder, an eyeliner, a mascara or a nail varnish.

36. A coloring agent comprising at least one compound of formula (I)

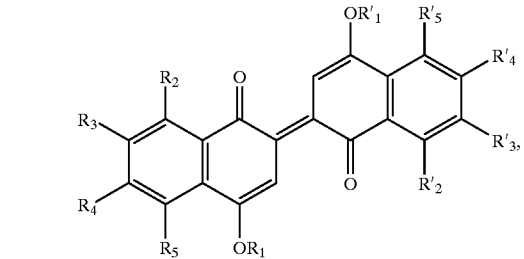

in which

R$_1$ and R'$_1$ are, independently of one another, saturated or unsaturated, linear, branched or cyclic alkyl radicals having 1 to 18 carbon atoms optionally substituted by at least one substituent chosen from halogens and hydroxyl radicals and optionally interrupted by one or more heteroatoms;

R$_2$, R'$_2$, R$_3$, R'$_3$, R$_4$, R'$_4$, R$_5$ and R'$_5$ are, independently of one another, chosen from a hydrogen atom, a halogenated radical, a hydroxyl radical and a saturated or unsaturated, linear or branched, alkyl, alkyloxy, acyl or acyloxy radical having 1 to 6 carbon atoms, at least one pulverulent material according to claim 24, or mixtures thereof.

37. A cosmetic composition comprising a coloring agent according to claim 36.

38. A method of coloring keratinous materials, mucous membranes or semi-mucous membranes comprising applying to said keratinous materials, mucous membranes or semi-mucous membranes at least one compound of formula (I)

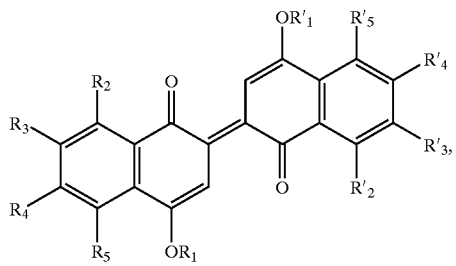

in which $R_1$ and $R'_1$ are, independently of one another, saturated or unsaturated, linear, branched or cyclic alkyl radicals having 1 to 18 carbon atoms optionally substituted by at least one substituent chosen from halogens and hydroxyl radicals and optionally interrupted by one or more heteroatoms;

$R_2$, $R'_2$, $R_3$, $R'_3$, $R_4$, $R'_4$, $R_5$ and $R'_5$ are, independently of one another, chosen from a hydrogen atom, a halogenated radical, a hydroxyl radical and a saturated or unsaturated, linear or branched, alkyl, alkyloxy, acyl or acyloxy radical having 1 to 6 carbon atoms, at least one pulverulent material according to claim 24, or mixtures thereof.

39. A method of making a pulverulent material comprising dissolving in an appropriate solvent at least one compound of formula (I):

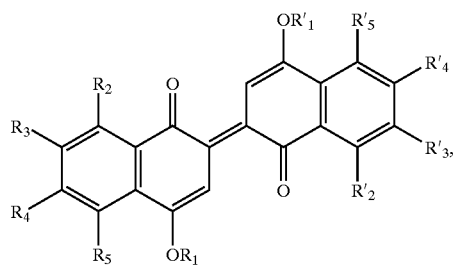

in which $R_1$ and $R'_1$ are, independently of one another, saturated or unsaturated, linear, branched or cyclic alkyl radicals having 1 to 18 carbon atoms optionally substituted by at least one substituent chosen from halogens and hydroxyl radicals and optionally interrupted by one or more heteroatoms;

$R_2$, $R'_2$, $R_3$, $R'_3$, $R_4$, $R'_4$, $R_5$ and $R'_5$ are, independently of one another, chosen from a hydrogen atom, a halogenated radical, a hydroxyl radical and a saturated or unsaturated, linear or branched, alkyl, alkyloxy, acyl or acyloxy radical having 1 to 6 carbon atoms, and precipitating said at least one compound of formula (I) on a substrate particle to be coated.

* * * * *